United States Patent [19]

Diefenbach

[11] 4,364,874

[45] Dec. 21, 1982

[54] METHOD OF MAKING ALUMINUM ALKYLS

[75] Inventor: Steven P. Diefenbach, Baton Rouge, La.

[73] Assignee: Ethyl Corporation, Richmond, Va.

[21] Appl. No.: 282,495

[22] Filed: Jul. 13, 1981

[51] Int. Cl.³ .............................................. C07F 5/06
[52] U.S. Cl. ............................................... 260/448 A
[58] Field of Search ................................... 260/448 A

[56] References Cited

U.S. PATENT DOCUMENTS

| | | | |
|---|---|---|---|
| 2,691,668 | 10/1954 | Liegler et al. | 260/448 A |
| 2,744,127 | 5/1956 | Liegler et al. | 260/448 A |
| 2,786,860 | 3/1957 | Liegler et al. | 260/448 A |
| 2,839,556 | 6/1958 | Liegler et al. | 260/448 A |
| 2,863,894 | 12/1958 | Smith | 260/448 A |
| 2,931,820 | 4/1960 | Barclay et al. | 260/448 A |
| 2,952,698 | 9/1960 | Neal et al. | 260/448 A |
| 4,116,992 | 9/1978 | Eidt | 260/448 A |
| 4,118,409 | 10/1978 | Eidt | 260/448 A |

*Primary Examiner*—Helen M. S. Sneed
*Attorney, Agent, or Firm*—Donald L. Johnson; John F. Sieberth; Paul H. Leonard

[57] ABSTRACT

A method of making aluminum alkyls utilizing an uncatalyzed exchange reaction wherein an aluminum trialkyl is reacted with an alkyl iodide in which the alkyl group differs from at least one of the alkyl groups of the aluminum trialkyl to form an aluminum trialkyl having the alkyl radical of the alkyl iodide reactant and an alkyl iodide having the alkyl radical of the aluminum trialkyl reactant. In particular, triethyl aluminum is reacted with methyl iodide to form trimethylaluminum and ethyl iodide. Aralkyl groups may be substituted for the alkyl groups to produce corresponding aralkyl compounds.

20 Claims, No Drawings

METHOD OF MAKING ALUMINUM ALKYLS

BACKGROUND OF THE INVENTION

Field of the Invention

The present invention relates to a method of making aluminum alkyls or alkyl aluminum compounds and especially to the making of trimethylaluminum.

A variety of processes are known for the preparation of aluminum alkyls and for the preparation of trimethylaluminum in particular. Decomposition reactions of aluminum alkyls with alkyl halides are documented in the literature.

One preferred method for making trimethylaluminum involves the sodium reduction of methylaluminum sesquichloride. Such procedure is an expensive one. Processes of this type are described in British Pat. No. 762,200 and U.S. Pat. No. 2,954,389 and in an article by A. V. Grosse and J. M. Mavity, *Journal of Organic Chemistry*, 5, 106 (1940). Preparation of trimethylaluminum has also been carried out by the sodium reduction of dimethylaluminum chloride as described in an article by S. Pasynkiewicz and M. Boleslawski, *Journal of Organometallic Chemistry*, 25, 29 (1970). The methods described in the foregoing articles each form a basis for existing commercial processes for the production of trimethylaluminum, but each produce non-usable by-products having limited value in vast quantities in comparison to the trimethylaluminum produced. The by-products produced by the above processes are aluminum and sodium chloride.

The several processes that have utilized the above sodium reduction reactions suffer from an inherent problem in that trimethylaluminum will itself react with sodium to produce sodium tetramethylaluminate, a compound that, unless it reacts with dimethylaluminum chloride will cause reduced yields and present a disposal problem. Sodium tetramethylaluminate is extremely reactive towards moisture in the air, as would excess unreacted sodium. The disposal problems presented by these two compounds represent a significant proportion of the cost of production of trimethylaluminum manufactured by such processes.

Although the conversion of dimethylaluminum chloride to trimethylaluminum without the use of sodium (Cryolite Process) is described in U.S. Pat. No. 2,839,556, this reaction scheme produces a vast amount of solid by-product having limited commercial value.

Two other methods for production of aluminum trialkyls are described in an article by R. Koster and P. Binger, *Advances in Inorganic and Radiochemistry*, I, 1263 (1965) and by K. S. Pitzer and H. S. Gutowsky, *Journal of American Chemical Society*, 68, 2204 (1946). Both of these methods suffer from the use of expensive starting materials and the production of non-useful or extremely reactive by-products requiring expensive process equipment and handling techniques.

U.S. Pat. No. 2,744,127 describes a relatively simple process for the preparation of trimethylaluminum which produces as a by-product magnesium chloride in the weight ratio 2.7:1 magnesium chloride:trimethylaluminum. The magnesium chloride has little or no commercial value.

A process for producing a mono-hydrocarbon aluminum dihalide is disclosed in U.S. Pat. No. 2,270,292. In such process, a hydrocarbon halide is reacted with metallic aluminum to form a di-hydrocarbon-aluminum-mono-halide and the latter is then reacted with an aluminum trihalide to form the desired dihalide product.

U.S. Pat. No. 2,863,894 relates to a process for producing aluminum alkyls, wherein aluminum is reacted with a primary alkyl halide, including methyl iodide in the presence of an inert, aromatic-free solvent to form a solution of sesquihalide dissolved in the inert solvent and then reacting the sesquihalide with an alkali metal to form the aluminum alkyl.

A more recent patent, U.S. Pat. No. 4,118,409, provides for jointly making trimethylaluminum and alkylaluminum bromides and iodides by mixing an aluminum trialkyl and a methylaluminum bromide or iodide and then distilling from the mixture trimethylaluminum as a first fraction and then alkylaluminum bromides or iodides as a subsequent fraction. The alkylaluminum halides used in such a redistribution process are themselves expensive compounds.

SUMMARY OF THE INVENTION

The present invention relates to a process for making alkyl aluminum compounds, wherein a trialkylaluminum compound is reacted with an alkyl iodide to form via an uncatalyzed exchange reaction a trialkylaluminum compound product having the alkyl radical of the alkyl iodide reactant and an alkyl iodide having the alkyl radical of the trialkylaluminum compound.

Aralkylaluminum compounds may also be made by such process by substituting an aralkyl iodide or triaralkylaluminum compound for the alkyl iodide or trialkylaluminum compound, respectively.

DESCRIPTION OF THE PREFERRED EMBODIMENTS

In the preferred form of the invention, trimethylaluminum is prepared by a thermal alkyl group exchange reaction between trialkylaluminum and methyl iodide. The following equation represents the reaction in general:

wherein
R=$C_2H_5$ to $C_{22}H_{45}$, and
R'=$CH_3$ to $C_{20}H_{41}$.

Of the trialkylaluminum compounds suitable for use in this invention, triethylaluminum is most preferred. Other preferred aluminum alkyl compounds are tri-n-propylaluminum, tri-n-butylaluminum, tri-iso-butylaluminum, trihexylaluminum and trioctylaluminum. Additional trialkylaluminum compounds which may be used as reactants in this invention are those compounds having up to 22 carbon atoms in the alkyl group. Comparable aralkylaluminum compounds may also be used.

Of the alkyl iodide compounds suitable for use in this invention, methyl iodide is most preferred. Other preferred iodides are ethyl iodide, iso-butyl iodide, and those alkyl iodides having up to 20 carbon atoms in the alkyl group.

The reaction may be carried out at a temperature of from about $-20°$ C. to about $200°$ C. and preferably from about $0°$ C. to about $150°$ C. The most preferred range is about $25°$ C. to about $100°$ C.

Generally, it takes about 18 to 24 hours for the exchange reaction to be completed. Higher temperatures usually provide shorter reaction times.

Although the reaction does not require a solvent, one may be desirable in some instances. Suitable solvents are hydrocarbon solvents, especially aromatic hydrocarbons such as benzene, toluene, and xylenes. Other suitable solvents are chlorinated hydrocarbons such as chlorobenzene and methyl chloride.

Basic ethers such as tetrahydrofuran, amines, amides and solvents bearing acidic protons are not suitable in the reaction of this invention.

When the alkyl group of the aluminum compound is ethyl and the alkyl iodide is methyl iodide, the exchange proceeds at 90° C. When the alkyl group is decyl or isobutyl, the reaction proceeds at 25° C. The exchange is quite selective and gives high conversion to trimethylaluminum. Similar reactions between other aluminum alkyls and alkyl iodides give a random exchange of alkyl groups with equilibrium constant (K) equal to about one ($\sim 1$).

The foregoing reaction offers an economically attractive synthetic route to the preparation of trimethylaluminum and/or long-chain alkyl iodides.

The foregoing described invention can be further understood by the following examples:

GENERAL

Reactants used were commercially available products and were used as received unless otherwise noted. Methyl chloride and all aluminum alkyl compounds were products of Ethyl Corporation. Methyl iodide and ethyl iodide were purchased from Aldrich. Isobutyl iodide and n-decyl iodide were purchased from Pfaltz and Bauer. Methyl bromide was obtained from Matheson. Cyclohexane was deoxygenated and stored over molecular sieves. Tetrahydrofuran was dried over calcium hydride and distilled under nitrogen before use. NMR (Nuclear Magnetic Resonance) spectra were recorded on a Varian EM-390 90 MHz spectrometer.

GENERAL PROCEDURE FOR ALUMINUM ALKYL-ALKYL IODIDE EXCHANGE REACTIONS

A Fisher Porter pressure vessel was charged in a nitrogen filled dry box with the appropriate quantities of alkyl iodide and aluminum alkyl (Table I). A few mole percent of cyclohexane was added as an internal NMR standard. At this point, the NMR spectrum of the initial solution was taken. The vessel was then capped with a plug containing a pressure gauge, thermocouple well and dip leg. The vessel was removed from the dry box and placed into an oil bath preheated to the desired temperature. After the appropriate time interval, the vessel was removed and cooled to room temperature. The work-up procedure was carried out in the dry box. A $\sim 1$ ml aliquot of the final reaction solution was filtered through a Millipore Swinnex filter disc containing a Mitex filter into an NMR tube. The products were determined from the NMR spectrum by comparison with authentic samples. Yields were determined by NMR integration vervus the cyclohexane standard.

Although not wishing to be bound by any particular theory, it is generally believed that an aluminum alkyl abstracts halide ion from an alkyl halide to generate an intermediate carbonium-counterion pair (e.g., $R^+R'_3AlX^-$) that has been envoked to account for the four typical reactions usually observed (i.e., reduction, alkylation, elimination and Friedel-Crafts alkylation). Methyl chloride and methyl bromide are virtually unreactive with triethylaluminum. Batalov and Korshanov have reported that an alkyl group exchange can be achieved between triethylaluminum and ethyl bromide with the aid of a metal halide catalyst.

TABLE I
ALUMINUM ALKYL-ALKYL IODIDE EXCHANGE $R_3Al + 3R'I \longrightarrow R'_3Al + 3RI$

| Run No. | R | R' | $\frac{[RI]}{[R_3Al]}$ | Conditions | $R'_3Al^a$ | $RI^a$ | Percent Exchange[b] |
|---|---|---|---|---|---|---|---|
| (1) | Et | Me | 3.31 | 25° C., 18 h. | Me$_3$Al | EtI | 11 |
| (2) | Et | Me | 4.41 | 92° C., 18 h. | Me$_3$Al | EtI | >95 |
| (3) | Et | n-decyl | 3.4 | 25° C., 18 h. | (n-decyl)$_3$Al | EtI | $\sim 50^d$ |
| (4) | Et | Ph | 3.3 | 118° C., 16 h. | | | 0 |
| (5) | i-Bu | Me | 9.7 | 25° C., 21 h. | Me$_3$Al | i-BuI | >95 |
| (6) | i-Bu | Et | 5 | 25° C., 18 h. | Et$_3$Al | i-BuI | $\sim 50^d$ |
| (7) | i-Bu | Me | 19.3 | 25° C., 18 h. (Et$_2$AlI)[c] | Me$_3$Al | i-BuI | 17 |
| (8) | i-Bu | MeI | 9.7 | 30° C., 18 h. (60 psig CO)[c] | | | 0 |
| (9) | i-Bu | MeI | 9.7 | 25° C., 72 h. (THF) | | | 0 |
| (10) | n-decyl | Me | 4.4 | 25° C., 18 h. | Me$_3$Al | n-decylI | >95 |
| (11) | n-decyl | Me | 4.4 | 60° C., 2 h. | Me$_3$Al | n-decylI | >95 |
| (12) | n-decyl | Ph | 3.3 | 60° C., 4 h. | | | N.R. |
| (13) | n-decyl | Et | 3.4 | 25° C., 18 h. | Et$_3$Al | n-decylI | $\sim 50^d$ |
| (14) | n-decyl | MeI | 3.1 | 25° C., 18 h. (Et$_2$AlCl)[c] | Me$_3$Al | EtI | 19 |
|   |   |   |   | 60° C., 18 h. (Et$_2$AlCl)[c] | Me$_3$Al | EtI | 38 |
| (15) | Et$_2$AlCl[e] | Me | 3.5[e] | 92° C., 18 h. | Et(Me)AlCl[e] | EtI | 95 |
| (16) | Et$_2$AlCl[e] | Me | 3.5[e] | 25° C., 66 h. | Et(Me)AlCl[e] | EtI | 40 |

[a]The products were determined from the NMR spectra by comparison with those from authentic samples.
[b]The percent exchange was calculated from the NMR integration vs a cyclohexane standard.
[c]These reactions were run in the presence of an excess of the indicated reagent.
[d]Only a rough approximation could be obtained due to the chemical shift similarities between products and reactants.
[e]Et$_2$AlCl substituted for R$_3$Al. Et(Me)AlCl substituted for R'$_3$Al.
Et = Ethyl (C$_2$H$_5$);
Me = Methyl (CH$_3$);
Ph = Phenyl (C$_6$H$_5$);
i-Bu = iso-Butyl (C$_4$H$_9$)

It has now been found that a different mode of reaction is observed with alkyl iodides (Table I). When trialkylaluminum is heated in the presence of methyl iodide, an alkyl group exchange reaction occurs without the aid of a catalyst to produce quantitative yields of trimethylaluminum and the corresponding alkyl iodide (Equation 1).

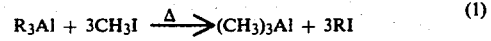

$$R_3Al + 3CH_3I \xrightarrow{\Delta} (CH_3)_3Al + 3RI \quad (1)$$

$R = C_2H_5$ to $C_{22}H_{45}$.

For $R = C_4H_9$ and $C_{10}H_{21}$, the reaction proceeds at 25° C. and is usually complete after ~18 hours. Higher temperatures shorten the reaction times. A temperature of ~90° C. is necessary when $R = C_2H_5$ to give moderate reaction rates. A stoichiometry of 3:1 MeI to $R_3Al$ was found in each case. Products and yields were determined from the NMR spectrum.

A similar reaction between i-Bu$_2$AlH and MeI proceeded at 25° C. to give ~47% yields (a ~1:1 equilibrium mixture) of i-BuI and i-Bu(Me)AlH (Equation 2). It is believed that the initial

$$i\text{-Bu}_2AlH + MeI \xrightleftharpoons{25°\ C.} i\text{-Bu(Me)AlH} + i\text{-BuI} \quad (2)$$

$$2i\text{-Bu(Me)AlH} \rightleftharpoons i\text{-Bu}_2AlH + Me_2AlH \quad (3)$$

product i-Bu(Me)AlH undergoes an exchange to give i-Bu$_2$AlH and Me$_2$AlH (Equation 3). This exchange is rapid at 25° C. making it difficult to distinguish i-Bu(Me)AlH from Me$_2$AlH. Almost identical yields were obtained when the reaction was run at 60° C. Reduction of MeI to CH$_4$ was not observed.

EXAMPLE 1

One mole of triethylaluminum was reacted with three moles of methyl iodide at 92° C. for 18 hours. Nearly quantitative yields of trimethylaluminum and ethyl iodide were obtained.

EXAMPLE 2

Using an excess of methyl iodide, the reaction was carried out with tri-isobutylaluminum at 25° C. for 21 hours. Quantitative yields of trimethylaluminum and isobutyl iodide were obtained.

EXAMPLE 3

Using an excess of methyl iodide, the reaction was carried out with tri-n-decyl aluminum at 25° C. for 18 hours. Quantitative yields of trimethylaluminum and n-decyl iodide were obtained.

EXAMPLE 4

Similar reactions using triethylaluminum, tri-isobutylaluminum or tri-n-decyl aluminum with excess phenyl iodide failed to produce any triphenylaluminum under a variety of conditions.

EXAMPLE 5

Similar reactions using tri-isobutylaluminum with an excess of methyl iodide in the presence of diethylaluminum iodide, 60 psig carbon monoxide or tetrahydrofuran failed to give exchange products. Unreacted starting materials were recovered.

EXAMPLE 6

Tri-n-decyl aluminum was reacted with methyl iodide in the presence of an excess of diethylaluminum chloride at 60° C. and yielded about 38% ethyl iodide and dimethylaluminum chloride and/or ethylmethylaluminum chloride.

EXAMPLE 7

Tri-isobutylaluminum was reacted with an excess of ethyl iodide at 25° C. with a 3:1 molar ratio of iodide to aluminum to give approximately 50 percent conversion to ethylaluminum bonds and 50 percent isobutyl iodide. An equilibrium was apparently reached, wherein $K \approx 1$.

EXAMPLE 8

Tri-n-decylaluminum was reacted with ethyl iodide similarly to Example 7. Similar 50 percent conversions to ethylaluminum bonds and n-decyl iodide ($K \approx 1$) were obtained.

EXAMPLE 9

Di-isobutylaluminum hydride was reacted with an excess of methyl iodide at 25° C. for 18 hours and gave ~47% yields of isobutyl iodide and isobutylmethylaluminum hydride. The latter may undergo exchange to produce di-isobutylaluminum hydride and dimethylaluminum hydride. Almost identical yields were obtained at 60° C. Reduction of methyl iodide to methane was not observed.

EXAMPLE 10

Diethylaluminum chloride was reacted with an excess of methyl iodide at 92° C. for 18 hours to give greater than 95 percent yields of ethyl iodide and ethylmethylaluminum chloride. The latter was in rapid equilibrium with diethylaluminum chloride and dimethylaluminum chloride. At 25° C., only a 40 percent exchange was observed.

EXAMPLE 11

Diethylaluminum iodide was reacted with an excess of methyl iodide at 85° C. The reaction was much slower than with diethylaluminum chloride and only 37 percent yields of ethylmethylaluminum iodide and ethyl iodide were obtained.

Additional reactions are summarized as follows:

Reaction of 4.4 moles of methyl iodide with one mole of tri-n-decylaluminum at 25° C. for 18 hours gave greater than 95 percent conversion to trimethylaluminum and n-decyl iodide. With adequate product separation, alkyl iodides of any chain length can be prepared.

When ethyl iodide is used as the alkyl halide, the exchange with trialkylaluminum compounds is about 50 percent complete for near stoichiometric amounts/reactants.

When ethyl iodide is reacted with tri-isobutylaluminum, exchange occurs at 25° C. to produce triethylaluminum and isobutyl iodide. Equilibrium is reached after about 18 hours. Degree of exchange is difficult to estimate accurately by NMR integration as there is a peak overlap; however, exchange is near 50 percent. The reaction proceeds more rapidly at 65° C. (about 4 hours to equilibrium), but long contact times (about 22 hours) at such temperatures apparently result in reactant losses.

Reacting ethyl iodide with tri-n-decyl aluminum at 25° C. for 18 hours proceeds to give triethylaluminum and decyl iodide at yields of about 50 percent. The equilibrium constant for this reaction at 25° C. is about one. The reaction of n-decyl iodide with triethylaluminum gives essentially the same composition. This clearly shows that the equilibrium constant for exchange is about one for ethyl versus n-decyl.

Uncatalyzed reactions using methyl chloride and methyl bromide as the alkyl halide and triethylaluminum and tri-isobutylaluminum were tried at temperatures up to 120° C. Tri-ethylaluminum did not react with either methyl chloride or methyl bromide. Tri-isobutylaluminum produced only gummy orange oils and no reaction at all with ethyl bromide at 25° C. and 65° C. A similar system utilizing triethylaluminum, aluminum trichloride and methyl chloride also failed to give exchange products at temperatures up to 95° C.

Following the usual exchange conditions, i.e., 18–24 hours at 95°–100° C., and using a tetrahydrofuran (THF) solvent, no exchange was detected when employing triethylaluminum and either methyl chloride or methyl bromide. Substituting tri-isobutylaluminum for triethylaluminum and using methyl iodide also resulted in no exchange.

The foregoing disclosure and description of the invention is illustrative and explanatory thereof and various changes may be made within the scope of the appended claims without departing from the spirit of the invention.

What is claimed is:

1. A method of making aluminum alkyl or aralkyl compounds comprising reacting a trialkyl or triaralkyl aluminum compound with an alkyl or aralkyl iodide in which the alkyl or aralkyl group differs from at least one of the alkyl or aralkyl groups of the trialkylaluminum compounds at a temperature of from about $-20°$ C. to about 200° C. to form via an uncatalyzed exchange reaction a trialkylaluminum compound product having the alkyl or aralkyl radical of the alkyl or aralkyl iodide reactant and an alkyl or aralkyl iodide having the alkyl or aralkyl radical of the trialkyl or triaralkylaluminum compound.

2. The method of claim 1, wherein the aluminum alkyl compound reactant is triethylaluminum and the alkyl iodide reactant is methyl iodide and the products formed are trimethylaluminum and ethyl iodide.

3. The method of claim 1, wherein the aluminum alkyl compound reactant is tri-isobutylaluminum and the alkyl iodide reactant is methyl iodide and the products formed are trimethylaluminum and isobutyl iodide.

4. The method of claim 1, wherein the aluminum alkyl compound reactant is tri-n-decylaluminum and the alkyl iodide reactant is methyl iodide and the products formed are trimethylaluminum and n-decyl iodide.

5. The method of claim 1, wherein the reaction is carried out at a temperature of from about 0° C. to about 150° C.

6. The method of claim 1, wherein the reaction is carried out at a temperature of about 95° C.

7. The method of claim 1, wherein the reaction is carried out at a temperature of about 25° C.

8. The method of claim 1, wherein the reaction is carried out up to about 24 hours.

9. The method of claim 1, wherein the reaction is carried out in the presence of a solvent selected from the group of hydrocarbon solvents and chlorinated aromatic solvents.

10. A method of making aluminum alkyl compounds comprising the following uncatalyzed reaction:

$$R_3Al + 3R'I \rightleftharpoons R'_3Al + 3RI$$

wherein
R = $C_2$–$C_{22}$ alkyl group and
R' = $C_1$–$C_{20}$ alkyl group different from R; and,
said reaction is carried out at a temperature of about $-20°$ C. to about 200° C.

11. The method of claim 10, wherein R is an ethyl group and R' is a methyl group.

12. The method of claim 10, wherein $R_3Al$ is $(CH_3)_2C_2H_5Al$ and R'I is $CH_3I$.

13. The method of claim 10, wherein $R_3Al$ is $CH_3(C_2H_5)_2Al$ and R'I is $CH_3I$.

14. The method of claim 10, wherein $R_3Al$ is $(C_2H_5)_3Al$ and R'I is $CH_3I$.

15. The method of claim 10, wherein $R_3Al$ is selected from the group consisting of tri-n-propylaluminum, tri-n-butylaluminum, tri-isobutylaluminum, tri-n-octylaluminum, and tri-n-decylaluminum and R'I is methyl iodide.

16. The method of claim 10, wherein $R_3Al$ is tri-isobutylaluminum and R'I is ethyl iodide and the exchange is statistical.

17. The method of claim 10, wherein $R_3Al$ is $R_2AlH$ and R'I is methyl iodide.

18. The method of claim 10, wherein $R_3Al$ is $R_2AlCl$ and R'I is methyl iodide.

19. The method of claim 10, wherein R'I is $C_6H_5(CH_2)_nI$ and n is an integer from 1 to 3.

20. The method of claim 1, wherein the alkyl group in the aluminum compound contains more carbon atoms than the alkyl group in the iodide.

* * * * *